United States Patent
Feng et al.

(10) Patent No.: US 9,029,603 B2
(45) Date of Patent: May 12, 2015

(54) PROCESS FOR PREPARING ALKYLATED P-PHENYLENEDIAMINES

(75) Inventors: Xiaogen Feng, Hangzhou (CN); Nongyue Wang, Hangzhou (CN); Xiaohui Mao, Lanxi (CN); Ruibiao Yu, Hangzhou (CN); Qianwen Cheng, Shanghai (CN)

(73) Assignee: Jiangsu Sinorgchem Technology Co., Ltd., Taizhou, Jiangsu Province (CN)

( * ) Notice: Subject to any disclaimer, the term of this patent is extended or adjusted under 35 U.S.C. 154(b) by 30 days.

(21) Appl. No.: 13/620,588

(22) Filed: Sep. 14, 2012

(65) Prior Publication Data

US 2013/0066113 A1 Mar. 14, 2013

Related U.S. Application Data

(60) Continuation of application No. 11/759,897, filed on Jun. 7, 2007, now Pat. No. 8,293,673, which is a division of application No. 11/477,954, filed on Jun. 30, 2006, now Pat. No. 7,235,694, which is a continuation of application No. 10/883,042, filed on Jul. 2, 2004, now Pat. No. 7,084,302.

(30) Foreign Application Priority Data

| Jul. 4, 2003 | (CN) | 03 1 48194 |
|---|---|---|
| Jul. 4, 2003 | (CN) | 03 1 48195 |
| Jul. 4, 2003 | (CN) | 03 1 48196 |
| Jul. 4, 2003 | (CN) | 03 1 48198 |
| Jul. 4, 2003 | (CN) | 03 1 48199 |
| Jul. 4, 2003 | (CN) | 03 1 48200 |
| Jul. 4, 2003 | (CN) | 03 1 48565 |
| Jul. 4, 2003 | (CN) | 03 1 48566 |

(51) Int. Cl.
*C07C 209/24* (2006.01)
*C07C 209/36* (2006.01)
(Continued)

(52) U.S. Cl.
CPC .............. *C07C 209/24* (2013.01); *B01D 1/065* (2013.01); *C07C 209/36* (2013.01); *C07C 209/02* (2013.01); *C07C 209/38* (2013.01); *C07C 209/86* (2013.01)

(58) Field of Classification Search
None
See application file for complete search history.

(56) References Cited

U.S. PATENT DOCUMENTS

| 2,635,100 A | 4/1953 | Werntz |
| 3,768,539 A | 10/1973 | Chamberline et al. |

(Continued)

FOREIGN PATENT DOCUMENTS

| CN | 1142985 A | 2/1997 |
| CN | 2294446 Y | 10/1998 |

(Continued)

OTHER PUBLICATIONS

Anonymously, Research Disclosure, Research Disclosure database No. 407033, published in the Mar. 1998 paper journal.*

(Continued)

*Primary Examiner* — Yun Qian
(74) *Attorney, Agent, or Firm* — Manni Li; Mei & Mark LLP

(57) ABSTRACT

A process for preparing alkylated p-phenylenediamine having the steps of reacting aniline and nitrobenzene in presence of a complex base catalyst to obtain 4-aminodiphenylamine intermediates, hydrogenating the 4-aminodiphenylamine intermediates to 4-aminodiphenylamine in presence of a hydrogenation catalyst, and reductively alkylating the 4-aminodiphenylamine to alkylated p-phenylenediamine.

18 Claims, 2 Drawing Sheets

(51) Int. Cl.
*C07C 29/60* (2006.01)
*B01D 1/06* (2006.01)
*C07C 209/02* (2006.01)
*C07C 209/38* (2006.01)
*C07C 209/86* (2006.01)

(56) References Cited

U.S. PATENT DOCUMENTS

| | | | |
|---|---|---|---|
| 3,797,552 A | 3/1974 | Frank et al. | |
| 3,875,988 A | 4/1975 | Machida et al. | |
| 4,072,713 A | 2/1978 | Bjornson | |
| 4,094,734 A | 6/1978 | Henderson | |
| 4,102,926 A | 7/1978 | Usvyatsov et al. | |
| 4,135,567 A | 1/1979 | Mattern | |
| 4,178,315 A | 12/1979 | Zengel et al. | |
| 4,187,248 A | 2/1980 | Merten et al. | |
| 4,287,365 A | 9/1981 | Becker et al. | |
| 4,313,002 A | 1/1982 | Symon et al. | |
| 4,404,401 A | 9/1983 | Zengel et al. | |
| 4,683,332 A | 7/1987 | Sturm | |
| 4,714,530 A | 12/1987 | Hale et al. | |
| 4,760,186 A | 7/1988 | Solodar | |
| 4,764,254 A | 8/1988 | Rosenblad | |
| 4,776,929 A | 10/1988 | Aoyama et al. | |
| 4,792,626 A | 12/1988 | Becher et al. | |
| 4,900,868 A | 2/1990 | Merten et al. | |
| 5,117,063 A * | 5/1992 | Stern et al. | 564/398 |
| 5,118,388 A | 6/1992 | Aboul-Nasr | |
| 5,253,737 A | 10/1993 | Klaue | |
| 5,331,099 A | 7/1994 | Stern et al. | |
| 5,420,354 A | 5/1995 | Malz et al. | |
| 5,438,034 A | 8/1995 | Walker | |
| 5,453,541 A | 9/1995 | Stern et al. | |
| 5,523,487 A | 6/1996 | Walker | |
| 5,552,531 A | 9/1996 | Stern et al. | |
| 5,608,111 A | 3/1997 | Stern et al. | |
| 5,633,407 A | 5/1997 | Stern et al. | |
| 5,739,403 A | 4/1998 | Reinartz et al. | |
| 5,840,982 A | 11/1998 | Reynolds et al. | |
| 5,925,791 A | 7/1999 | Buysch et al. | |
| 5,932,768 A | 8/1999 | Ooms et al. | |
| 5,973,206 A | 10/1999 | Laitinen | |
| 5,977,411 A | 11/1999 | DeVera | |
| 5,985,231 A | 11/1999 | Filippi et al. | |
| 5,994,584 A | 11/1999 | Ooms et al. | |
| 6,043,394 A | 3/2000 | Langer et al. | |
| 6,137,010 A | 10/2000 | Joo et al. | |
| 6,140,538 A | 10/2000 | Rains et al. | |
| 6,316,673 B2 | 11/2001 | Giera et al. | |
| 6,365,745 B1 | 4/2002 | Matsui et al. | |
| 6,368,996 B1 | 4/2002 | Mu et al. | |
| 6,388,136 B1 | 5/2002 | Beska et al. | |
| 6,395,933 B1 * | 5/2002 | Triplett et al. | 564/420 |
| 6,395,934 B1 | 5/2002 | Wegener et al. | |
| 6,403,852 B1 | 6/2002 | Yamamoto et al. | |
| 6,414,192 B1 | 7/2002 | Schelhaas et al. | |
| 6,423,872 B2 | 7/2002 | Marion | |
| 6,495,723 B1 | 12/2002 | DeVera et al. | |
| 6,583,320 B2 | 6/2003 | Triplett, II et al. | |
| 6,656,327 B2 | 12/2003 | Salmisuo | |
| 6,680,280 B1 | 1/2004 | Birke et al. | |
| 7,112,262 B2 | 9/2006 | Bethge | |
| 7,157,605 B2 | 1/2007 | Kim et al. | |
| 7,176,333 B2 | 2/2007 | Wang et al. | |
| 7,189,684 B2 | 3/2007 | Ohno et al. | |
| 7,989,662 B2 | 8/2011 | Feng et al. | |

| | | |
|---|---|---|
| 2002/0055652 A1 | 5/2002 | Schelhaas et al. |
| 2003/0088127 A1 | 5/2003 | Triplett et al. |
| 2006/0258887 A1 | 11/2006 | Kim et al. |

FOREIGN PATENT DOCUMENTS

| | | |
|---|---|---|
| CN | 1312400 A | 9/2001 |
| CN | 1437573 A | 8/2003 |
| CN | 1721391 A | 1/2006 |
| CN | 101277923 A | 10/2008 |
| DE | 19709124.5 | 9/1998 |
| DE | 19734055.5 | 2/1999 |
| DE | 19810929.6 | 9/1999 |
| EP | 184914 | 6/1986 |
| EP | 0148145 B1 | 12/1986 |
| EP | 0147379 B1 | 7/1987 |
| EP | 0566783 A1 | 4/1992 |
| EP | 784049 A1 | 7/1997 |
| FR | 2409979 | 6/1979 |
| GB | 947082 | 1/1964 |
| GB | 1198508 A | 7/1970 |
| GB | 2015998 A | 9/1979 |
| JP | 62-062814 A | 3/1987 |
| JP | 6306020 A | 11/1994 |
| JP | 6306021 A | 11/1994 |
| JP | 7-165682 A | 6/1995 |
| JP | 10-07627 A | 1/1998 |
| JP | 11-228506 A | 8/1999 |
| JP | 2001192701 A | 7/2001 |
| JP | 2001316337 A | 11/2001 |
| JP | 2002249467 A | 9/2002 |
| WO | WO 93/00324 | 1/1993 |
| WO | WO 94/25425 | 11/1994 |
| WO | WO 98/56751 | 12/1998 |
| WO | WO 99/28028 | 6/1999 |
| WO | WO 99/59956 | 11/1999 |
| WO | WO 00/51728 | 9/2000 |
| WO | WO 03/010126 | 2/2003 |
| WO | WO 03/075332 A | 12/2003 |

OTHER PUBLICATIONS

Wohl, A., Chemische Berichte 34:2442-2450 (1901).
Wohl, A., Chemische Berichte 36:4135-4138 (1903).
Fan, "4-Nitrosodiphenylamine," Organic Synthetic Dictionary, Beijing University of Science and Engineering Publication House, (Oct. 2003).
Wei et al., "New Method for Making p-Nitrodiphenylamine," Chemical Report, No. 10 (1996).
Zhu et al., "Study on Hydrogenation of Nitrodyphenylamine in Alkalescence System," Journal of Nanjing University of Technology, vol. 24, No. 6, pp. 48-51 (Nov. 2002).
Stern et al., "Direct Coupling of Aniline and Nitrobenzene: A New Example of Nucleophilic Aromatic Substitution for Hydrogen," J. Am. Chem. Soc. 114:9237-9238 (1992).
Stern et al., "Eliminating Chlorine in the Synthesis of Aromatic Amines: New Routes Which Utilize Nucleophilic Aromatic Substitution for Hydrogen," New J. Chem. 20:259-268 (1996).
Stern, "Chap. 11, Nucleophilic Aromatic Substitution of Hydrogen," ACS Symposium Series 577, Benign by Design (Aug. 1993).
Dickneider, "A Green Chemistry Module," website printout of Nov. 2003, http://academic.scranton.edu/faculty/CANNM1/advancedorganic/advancedorganicmodule.htm.
M. Makosza, "Phase transfer catalysis. A general green methodology in organic synthesis," Pure Appl. Chem., vol. 72, No. 7 (2000).
Dai, Tingfeng et al., Fine Petrochemistry, vol. 2 (1998).
Zhang, Zhongmin et al., Jiangxi Chemical Engeering, vol. 2 (1996).
Goldman, J. Org. Chem., 1969, vol. 34, No. 6, pp. 1979-1981 (Jun. 1969).

* cited by examiner

US 9,029,603 B2

1

PROCESS FOR PREPARING ALKYLATED P-PHENYLENEDIAMINES

CROSS-REFERENCE TO RELATED APPLICATIONS

The present application is a continuation of U.S. patent application Ser. No. 11/759,897 filed on Jun. 7, 2007, now allowed, which is a divisional of U.S. patent application Ser. No. 11/477,954 filed on Jun. 30, 2006 and issued as U.S. Pat. No. 7,235,694 on Jun. 26, 2007, which in turn is a continuation of U.S. Pat. No. 7,084,302 issued on Aug. 1, 2006, which claims priority on CN03148566.9, CN03148195.7, CN03148194.9, CN03148199.X, CN03148565.0, CN03148200.7, CN03148198.1, and CN03148196.5, all filed on Jul. 4, 2003 in China. The contents of all above-mentioned priority applications and patents are incorporated herein by reference in the entirety and for all purposes.

TECHNICAL FIELD

The present invention relates to a process for preparing alkylated p-phenylenediamines using nitrobenzene and aniline as the starting materials.

BACKGROUND OF THE INVENTION

4-Aminodiphenylamine is an important intermediate of antioxidant and stabilizer and an important chemical product for rubber industry and polymer industry. 4-aminodiphenylamine can be reductively alkylated by the well known methods to make alkylated p-phenylenediamines. Depending on the starting materials, known methods for preparing 4-aminodiphenylamine include:

(1) aniline method, where p-nitro-chlorobenzene and aniline as raw materials react in the presence of a catalyst to produce 4-nitrodiphenylamine, then, 4-nitrodiphenylamine is reduced by sodium sulfide to form 4-aminodiphenylamine;

(2) formanilide method, where formic acid and aniline are used as starting materials to prepare formanilide, which in turn reacts with p-nitro-chlorobenzene in the presence of an acid-binding agent such as potassium carbonate, to produce 4-nitrodiphenylamine, and then, 4-nitrodiphenylamine is reduced by sodium sulfide to form 4-aminodiphenylamine;

(3) diphenylamine method, where diphenylamine as raw material is nitrosated using a nitrite in an organic solvent to produce N-nitrosodiphenylamine, which is rearranged to 4-nitrosodiphenylamine hydrochloride under the action of anhydrous hydrogen chloride, and then, 4-nitrosodiphenylamine hydrochloride is neutralized with a base to give 4-nitrosodiphenylamine which is finally reduced to 4-aminodiphenylamine by sodium sulfide.

Although these methods use different starting materials, sodium sulfide is usually used as the reducing agent to prepare 4-aminodiphenylamine. These reactions suffer from severe reaction conditions, complex operation, high energy consumption, low yield, high cost, and environment pollution caused by concomitant waste water, waste gas, and waste residues.

Among the preparation methods for 4-aminodiphenylamine, some methods use nitrobenzene, nitrobenzene and aniline, or nitrosobenzene as raw materials to carry out condensation reaction, and then use hydrogen gas to perform hydrogenation to produce 4-aminophenylamine. In fact, it was reported in 1901 (Wohl, *Chemische Berichte* 34, p. 2442 (1901)) and 1903 (Wohl, *Chemische Berichte* 36, p. 4135 (1903)) that nitrobenzene reacted with aniline under the

2 action of a base to form 4-nitrosodiphenylamine and 4-nitrodiphenylamine. However, the method had been neither regarded as important nor developed because of the relative low yield until 1990s when it was researched and developed again and achieved some progress. See DE 19734055.5, DE 19810929.6, and DE 19709124.5. However, the methods as disclosed in the art have disadvantages.

First, the catalysts used in these methods are expensive, which results in relatively high production cost in an industrial-scale production. Thus, these methods have no advantage over other conventional methods. For examples, tetraalkyl ammonium hydroxide and fluoride used in condensation reaction and noble metal, such as palladium, platinum, rhodium, and the like, used in hydrogenation reaction are expensive. The instability of tetraalkyl ammonium hydroxide imparts some difficulty to the recovery and reuse of tetraalkyl ammonium hydroxide. In addition, the use of noble metal hydrogenation catalysts applies higher requirements to raw materials and equipment. Second, the yield is relatively low, which makes the methods only suitable for laboratory research. This is why these methods have been difficult to be industrially applied. Third, the operation is complicated. These methods are not in favor of continuous operations, which limits the production scale. Fourth, separation is difficult and purity of product is not high.

U.S. Pat. No. 6,395,933 discloses a process for synthesizing 4-aminodiphenylamine by reacting nitrobenzene and a substituted aniline at a certain temperature in the presence of a strong base and a phase-transfer catalyst. The process is not satisfactory in yields, and there are many side reactions. In the product mixture of 4-nitrodiphenylamine and 4-nitrosodiphenylamine, the proportion of 4-nitrodiphenylamine is too high which indicates that too much hydrogen has been consumed during the hydrogenation reaction and the production cost is thereby significantly increased. Furthermore, the process needs an oxidizing agent, which makes it unsuitable for industrial production.

WO 93/00324 discloses a process for preparing 4-aminodiphenylamine by reacting nitrobenzene and aniline at a proper temperature in a proper solvent in the presence of a base with the contents of proton materials in solution being controlled. The process requires a solvent and the control of the contents of proton materials in the solution. The introduction of the solvent results in increased energy consumption and difficulty for separation. Controlling the contents of proton materials gives rise to difficulty for operation and control of the reaction. In particular, at a later stage of the condensation reaction, controlling the contents of proton materials, which mainly means dehydration to lower water content, prolongs the reaction time and causes partial aniline to be entrained out. The later stage, the more difficult removing the proton materials. Controlling the proton materials at a certain range is difficult, and goes against industrial production. The expensive tetraalkyl quaternary amine base catalyst will quickly decompose in the course of controlling the contents of proton materials to a range of from 0.5 to 4 percent, resulting in increased production cost.

SUMMARY OF THE INVENTION

The present invention provides a continuous process for preparing 4-aminodiphenylamine and alkylated p-phenylenediamines, which uses nitrobenzene and aniline as the starting materials, a complex base catalyst as a condensation catalyst, and a powdery composite catalyst as a hydrogena tion catalyst. The process of the present invention for making 4-aminodiphenylamine comprises five stages:

1. condensation;
2. hydrogenation in the presence of a hydrogenation solvent;
3. separating, recovering, and reusing the complex base catalyst, and separating, recovering, and reusing the powdery composite catalyst which is optionally at least partially regenerated;
4. separating, recovering, and reusing aniline, and optionally, separating, recovering and reusing the hydrogenation solvent;
5. refining.

The present invention uses inexpensive catalysts with good yields in condensation and hydrogenation reaction and provides a process suitable for industrial scale production and continuous production of 4-aminodiphenylamine. Then, 4-aminodiphenylamine is reductively alkylated by known methods to make alkylated p-phenylenediamines.

DETAILED DESCRIPTION OF THE INVENTION

In following descriptions of the process of the present invention, Separation I refers to separating, recovering, and reusing a complex base catalyst, and separating, recovering, and reusing a powdery composite catalyst which is optionally at least partially regenerated; Separation II refers to separating, recovering, and reusing aniline, and optionally separating, recovering, and reusing hydrogenation solvent.

The expression "optionally separating, recovering, and reusing hydrogenation solvent" as used herein means that, when water is used as a hydrogenation solvent, water is optionally recovered and reused, and when an alcohol solvent, which will be described herein below, is used as a hydrogenation solvent, the alcohol hydrogenation solvent is separated, recovered, and reused.

Figure 1:
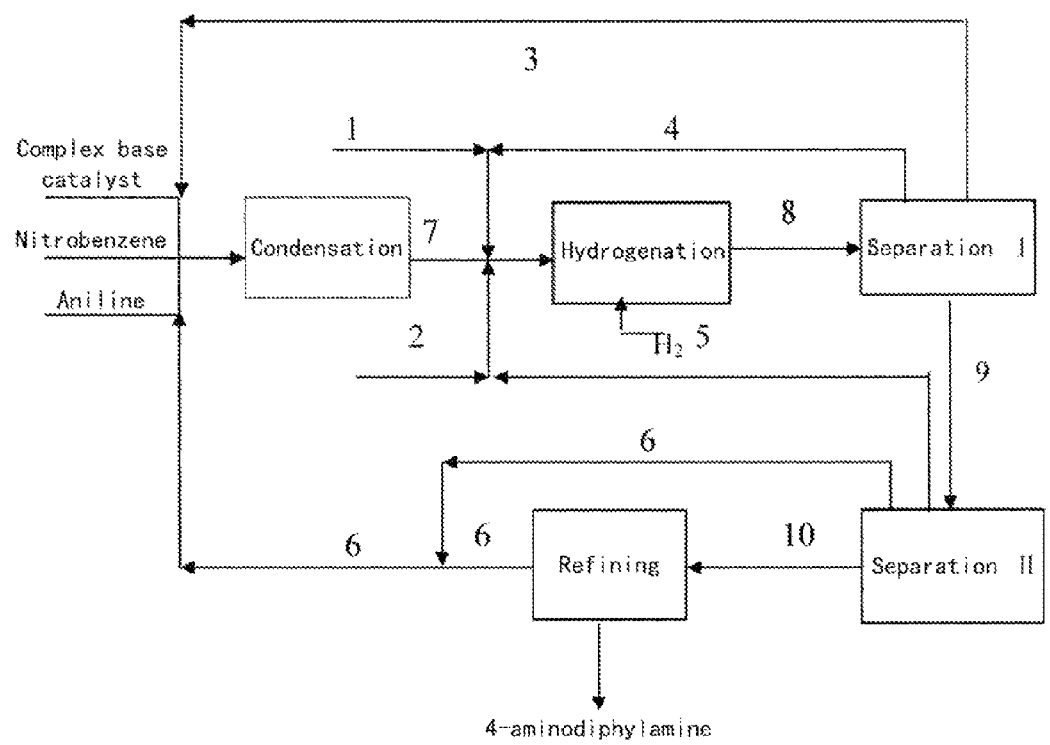
FIG. 1 is a flow chart showing an embodiment of the present invention for preparing 4-aminodiphenylamine. The reference numbers are: 1—powdery composite catalyst; 2—hydrogenation solvent; 3—reused complex base catalyst; 4—reused, optionally at least partially regenerated, powdery composite catalyst; 5—reused hydrogenation solvent; 6—reused aniline; 7—condensation liquid; 8—hydrogenation liquid; 9—aqueous phase obtained by evaporation in concentration process and organic phase obtained by extraction; 10—crude product of 4-aminodiphylamine.

With reference to FIG. 1, the process for preparing 4-aminodiphenylamine according to the present invention comprises the steps of:

continuously feeding nitrobenzene, aniline and a complex base catalyst, at desired proportion, to the condensation process stage reactor via metering pumps, and allowing them to react to form a condensation liquid (7) containing 4-nitrodiphenylamine, 4-nitrosodiphenylamine and/or salts thereof;

continuously feeding the condensation liquid (7) and hydrogenation solvent, including supplementary hydrogenation solvent (2) and optionally recovered hydrogenation solvent (5), at desired proportion to hydrogenation process stage reactor, and allowing them to react with hydrogen gas under the catalytic action of a powdery composite catalyst, including supplementary powdery composite catalyst (1) and reused, optionally regenerated, powdery composite catalyst (4), to form a hydrogenation liquid (8) containing 4-aminodiphenylamine;

feeding the hydrogenation liquid (8) to separation I process stage reactor, where (a) powdery composite catalyst (4), which is to be recycled back to the hydrogenation process stage reactor directly or after being at least partially regenerated, (b) complex base catalyst (3), which is to be recycled back to the condensation process stage reactor, and (c) aqueous phase obtained by evaporation during concentration and organic phase obtained by extraction (9) are obtained;

feeding separately the aqueous phase and the organic phase (9) obtained in separation I process stage reactor to separation II process stage reactor, where (a) aniline (6), which is to be recycled back to the condensation process stage reactor, (b) crude 4-aminodiphenylamine from which most aniline has been separated, and (c) optionally, hydrogenation solvent (5), which is to be recycled back to the hydrogenation process stage reactor, are obtained; and feeding crude 4-aminodiphenylamine (10) to refining process stage reactor, where (a) partial aniline (6), which is to be recycled back to the condensation process stage reactor, and (b) finished 4-aminodiphenylamine are obtained. The entire process is conducted continuously.

(1) Condensation.

In the condensation reaction, the molar ratio of nitrobenzene to aniline may be in the range of from 1:1 to 1:15. The reaction temperature may be in the range of from 20 to 150° C., preferably from 50 to 90° C. The reaction temperature is controlled to be no higher than 90° C. in order to keep the decomposition rate of the complex base catalyst for the condensation reaction to less than 0.5%. The reaction pressure may vary from 0.005 to 0.1 MPa (absolute pressure). The residence time of the feedstock in the entire condensation reactor is in the range of from 3.5 hours to 6 hours.

The complex base catalyst for the condensation reaction comprises tetraalkyl ammonium hydroxide, alkali metal hydroxide, and tetraalkyl ammonium salt. The complex base catalyst optionally comprises water. The total concentration of tetraalkyl ammonium hydroxide, alkali metal hydroxide, and tetraalkyl ammonium salt is in the range of from 10 to 100 percent by weight, preferably from 25 to 38 percent by weight, and the molar ratio of tetraalkyl ammonium hydroxide to alkali metal hydroxide to tetraalkyl ammonium salt is (0-9):(0.5-3):(0.5-3). The combination of tetraalkyl ammonium hydroxide with inexpensive alkali metal hydroxide or oxide and tetraalkyl ammonium salt can achieve the same goal as those obtained in the prior art where highly purified tetraalkyl ammonium hydroxide alone is used as catalyst. In the condensation reaction mixture, the molar ratio of hydroxide ion in complex base catalyst to nitrobenzene is in the range of from 1:4 to 4:1.

The complex base catalyst used in the condensation reaction is prepared as follows: tetraalkyl ammonium hydroxide, alkali metal hydroxide or oxide, and tetraalkyl ammonium salt, at desired molar ratio, are stirred in water at a temperature of from 0 to 90° C. until being homogeneous, to form an aqueous form of the complex base catalysts. Then water can be completely removed by adding benzene through azeotropic process, to form an anhydrous form of the complex base catalyst. The tetraalkyl ammonium hydroxide, alkali metal hydroxide or oxide, and tetraalkyl ammonium salt as raw materials may be in solid form or in aqueous solution form.

The complex base catalyst used in the present invention is particularly advantageous for carrying out the reaction, because the catalyst does not need to be constantly replenished. In the course of industrial production, the condensation reaction mixture unavoidably contacts with carbon dioxide and carbon monoxide which are present in both ambient air and hydrogen, which causes tetraalkyl ammonium hydroxide to be converted to tetraalkyl ammonium carbonate and decrease in the amount. In the case that only tetraalkyl ammonium hydroxide is used as the catalyst, the conversion of tetraalkyl ammonium hydroxide to ammonium salt decreases the quantity of the catalyst so that there is a constant need to supply the catalyst and get rid of the ammonium salt. In contrast, the present invention does not need any complex technology to supply tetraalkyl ammonium hydroxide and remove ammonium salt. The present invention provides that by increasing the contents or ratio of the alkali metal hydroxide or oxide in the complex base catalyst, the complex base catalyst retains the high catalytic reactivity in the presence of carbon dioxide and carbon monoxide during the reaction.

According to the present invention, nitrobenzene and aniline are condensed to form 4-nitrodiphenylamine and 4-nitrosodiphenylamine and/or their salts using the complex base catalyst at certain conditions. Anhydrous complex base catalyst may be used to convert nitrobenzene and aniline to 4-nitrodiphenylamine and 4-nitrosodiphenylamine and/or their salts in the condensation reaction according to the present invention. The selectivity and conversion of the reaction attain to the desired level at an anhydrous condition.

By using the complex base catalyst disclosed in the present invention, it is possible to avoid tight control of the proton materials, such as water, methanol, and the like, in the mixture, thus avoiding as much as possible the loss of the complex base catalyst and operation complexity due to the tight control of the proton materials. Without limited to any specific theory, it is believed that the integrated action of tetraalkyl ammonium hydroxide, alkali hydroxide, and tetraalkyl ammonium salt in the complex base catalyst gives such a result, thereby reducing the difficulty of operating and controlling the reaction. It is believed that the use of the complex base catalyst comprising tetraalkyl ammonium hydroxide, alkali hydroxide, and tetraalkyl ammonium salt makes the control of proton materials, for example water, in the reaction system unimportant. That is to say, condensation reaction can be carried out and the conversion and selectivity are not affected no matter whether there are no proton materials such as water in the solution or there are high contents of proton materials such as water in the solution. Thus, the difficulty of operating and controlling the reaction can be reduced and quantity of aniline entrained out by azeotropic dehydration can be decreased, so that the process is more suitable for industrial scale production.

In the process according to the present invention, the proton materials such as water no longer constitute a restricting factor of the reaction, and the selectivity and conversion can attain the desired level whether or not there are proton materials such as water. Furthermore, it has been found that the decomposition ratio of the complex base catalyst is lower than that of the single tetraalkyl ammonium hydroxide being used.

In a preferred embodiment of the present invention, condensation reaction can be carried out in a falling film reactor. In the reaction, nitrobenzene, aniline, and the complex base catalyst in desired proportion are continuously fed to a falling film reactor via a metering pump to be heated and allowed to condense. The condensation liquid in the falling film reactor is discharged from the bottom of the reactor into a first reactor to continue condensation reaction. A part of the condensation liquid from the bottom of the first reactor is conveyed back to the falling film reactor via a circulating pump to establish a local circulating system of the condensation reaction according to the present invention. The circulating system is mainly consisted of the falling film reactor and the first reactor, and the reactants continuously circulate via the condensation circulating pump. The circulating process maintains a level of condensation liquid that is sufficient to form a uniform film in the falling film reactor. The falling film reactor may utilize ethanol vapor, hot water, steam or methanol vapor, preferably ethanol vapor as heat medium, to make the temperature of the system very homogeneous and avoid local overheating. That there is hardly back-mixing of reaction liquid in the falling film reactor significantly decreases the chance of contact between the reaction product and the raw materials and minimizes the side reactions. The local circulating system including the falling film reactor enhances the condensation reaction rate and reduces the reaction time, which is shortened from more than ten hours to 3.5-6 hours.

It has also been found that continuous film reaction is higher than complete mixing reaction in both selectivity and yield. During this reaction, nitrobenzene reacts with aniline to form 4-nitrosodiphenylamine, nitrobenzene can also react with 4-nitrosodiphenylamine to form 4-nitrodiphenylamine, and nitrobenzene itself is reduced to nitrosobenzene, which in turn can react with aniline to form azobenzene. The latter reaction goes against main reaction and reduces the selectivity of the reaction. At the beginning of reaction, the quantity of nitrobenzene is relatively higher. Nitrobenzene is gradually converted to 4-nitrosodiphenylamine and the quantity of nitrobenzene becomes lower along with the reaction. The use of the continuous falling film reactor reduces the contact and reaction between nitrobenzene added and 4-nitrosodiphenylamine which is later formed (when the reactants enter the reactor to react, the concentration of nitrobenzene is relatively higher yet the concentration of 4-nitrosodiphenylamine is relatively lower, while at the end of the reaction, the concentration of 4-nitrosodiphenylamine is relatively higher yet the concentration of nitrobenzene is relatively lower), as well as the opportunity that nitrobenzene is reduced to nitrosobenzene by 4-nitrosodiphenylamine, thereby reducing reaction between nitrobenzene and aniline to form azobenzene.

In the condensation reaction of nitrobenzene and aniline in the presence of the complex base catalyst, the main side reaction is formation of by-products, azobenzene and phenazine. It is found that the higher the quantity of aniline, the less the side reaction to convert nitrobenzene to phenazine. Another by-product in the reaction is azobenzene. Azobenzene can be easily transformed into aniline at the hydrogenation process stage, so that it can be reused in the production. Therefore, the molar ratio of nitrobenzene to aniline used in the invention is selected as from 1:1 to 1:15.

Furthermore, in the process of the present invention, condensation reaction can be performed under proper ratio of nitrobenzene and aniline without the introduction of any solvent into the system and a good yield can be achieved.

The present invention improves the yield of the condensation reaction and makes the reaction moving towards desired direction utilizing the above method.

Those skilled in the art can contemplate that the condensation reaction according to the present process might employ multiple stages of reactors in series.

In the condensation process stage, it is unavoidable to lose part of the complex base catalyst along with the reaction. It is possible to supply only alkali metal hydroxide component and tetraalkyl ammonium salt component of the complex base catalyst when replenishing the catalyst, and their molar ratio is in the range of from 4:1 to 1:4. Alkali metal oxide can be used to replace alkali metal hydroxide, and its amount can be gotten by conversion of corresponding hydroxide to oxide.

The tetraalkyl ammonium salts useful in the present invention can be represented by a general formula of

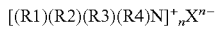

$[(R1)(R2)(R3)(R4)N]^+{}_n X^{n-}$ wherein R1, R2, R3 and R4, which may be identical or different, can be alkyl having from 1 to 4 carbon atoms, said alkyl can carry a hydrophilic substitute selected from the group consisting of hydroxy, methoxy, polyether, cationic polyamide, polyester, polyethylene polyamine, highly water-soluble quaternary ammonium salt-containing radical, etc., $X^{n-}$ is selected from the group consisting of halide ion, sulfate radical, carbonate radical, phosphate radical, bicarbonate radical, bisulfate radical, $C_1$-$C_2$-alkyl carbonate radical, $C_1$-$C_2$-alkyl sulfate radical, etc., and n is a value of from 1 to 2. Examples of the tetraalkyl ammonium salts include, but not limited to, poly-methylated triethylene tetraamine sulfate, poly-methylated diethylene triamine carbonate, N,N-dimethyl-N,N-bis(methoxyethyl) ammonium carbonate, N-methyl-N,N,N-tri(methoxyethyl) ammonium carbonate, N,N,N-trimethyl-N-hydroxyethyl ammonium carbonate, trimethyl hydroxyethyl ammonium chloride, N,N,N-trimethyl-N-ethoxylated (1-4 moles of ethylene oxide) ethyl ammonium carbonate, N,N,N-trimethyl-N-ethoxylated (1-4 moles of ethylene oxide) propyl ammonium carbonate, N,N,N-trimethyl-N-ethoxylated (1-4 moles of ethylene oxide) propyl ammonium chloride, N,N-dimethyl-N,N-bis(ethoxylated (1-4 moles of ethylene oxide) propyl) ammonium carbonate, tetramethyl ammonium carbonate, tetramethyl ammonium methyl-carbonate, tetraethyl ammonium carbonate, tetraethyl ammonium ethyl-carbonate, tetramethyl ammonium sulfate, tetramethyl ammonium methyl-sulfate, tetraethyl ammonium sulfate, and tetraethyl ammonium ethyl-sulfate.

The tetraalkyl ammonium hydroxide used in the complex base catalyst can be represented by a formula of

$R'_4 N^+ OH^-$, wherein R' is independently an alkyl having one or two carbon atoms. The tetraalkyl ammonium hydroxide may be prepared from corresponding tetraalkyl ammonium salt and base in polar solvent according to a process known per se.

The alkali metal hydroxides or oxides include hydroxides and oxides of lithium, sodium, potassium and rubidium, such as sodium hydroxide, potassium hydroxide, lithium hydroxide, sodium oxide or potassium oxide.

The tetraalkyl ammonium alkyl-carbonates or tetraalkyl ammonium alkyl-sulfates useful in the present invention can be prepared by the reaction of trialkyl amine and dialkyl ($C_1$-$C_2$) carbonate or dialkyl($C_1$-$C_2$) sulfate in polar solvent.

According to the present invention, the reaction temperature for the preparation of tetraalkyl ammonium alkyl-carbonate or tetraalkyl ammonium alkyl-sulfate varies from 50 to 200° C., preferably from 60 to 150° C., and reaction pressure varies from 0.1 to 3 MPa (gauge pressure). In general, the pressure depends on the selected temperature, type and amount of the solvent, namely, the less the amount of solvent, the higher the system pressure; and the higher the temperature, the higher the pressure. In the invention, the reaction pressure is preferably controlled in a range of from 0.4 to 2 MPa to obtain higher product yield.

In the reaction for the preparation of tetraalkyl ammonium alkyl-carbonate or tetraalkyl ammonium alkyl-sulfate according to the present invention, the molar ratio of trialkyl amine to dialkyl($C_1$-$C_2$) carbonate or dialkyl($C_1$-$C_2$) sulfate is selected as from 2:1 to 1:2. If the proportion of trialkyl amine is too high, then trialkyl amine will be superabundant in the reaction system and thus impose operational difficulty to subsequent processes and pollutes the environment. If the proportion of trialkyl amine is too low, then dialkyl($C_1$-$C_2$) carbonate or dialkyl($C_1$-$C_2$) sulfate will be superabundant, and thus cause the loss of dialkyl($C_1$-$C_2$) carbonate or dialkyl ($C_1$-$C_2$) sulfate in the subsequent reaction, thereby increasing the production cost.

In the process for the preparation of tetraalkyl ammonium alkyl-carbonate or tetraalkyl ammonium alkyl-sulfate according to the present invention, reaction time of trialkyl amine and dialkyl($C_1$-$C_2$) carbonate or dialkyl($C_1$-$C_2$) sulfate is in a range of from 1.5 to 6 hours. At the initial stage of the reaction, the reaction rate is high, and exothermic phenomenon is obvious. With consumption of raw materials, the reaction slows down and heat release is gradually reduced. During the reaction, the amount of cooling water is continuously adjusted to keep reaction temperature and pressure in a certain range.

The polar solvents useful in the condensation reaction according to the present invention include methanol, ethanol, or isopropyl alcohol. The amount of solvents used varies from 1 to 10 times of weight of trialkyl amine.

(2) Hydrogenation.

In the hydrogenation reaction of the present invention, hydrogen gas can be used as the reducing agent. The reaction temperature is in the range of from 50 to 100° C. The reaction pressure is in the range of from 0.2 to 3.0 MPa (absolute pressure). The reaction time varies from 2 hours to 7 hours. The volume ratio of gas to liquid is in the range of from 10:1 to 1500:1; the weight ratio of solid to liquid is in the range of from 0.5:100 to 16:100. The gas refers to the hydrogen gas; the liquid refers to the hydrogenation solvent and the condensation liquid; the solid refers to the powdery composite catalyst.

In the present invention, alcohols and/or water can be used as hydrogenation solvent. Among alcohols, methanol, ethanol, and isopropyl alcohol are preferred. The hydrogenation solvent can be used in such an amount that the weight ratio of the hydrogenation solvent to the condensation liquid is in the range of from 1:10 to 5:10. When an alcohol is used as the hydrogenation solvent, the alcohol need to be separated, recovered, and recycled. When water is used as the hydrogenation solvent, the aqueous phase after extraction as described herein below, is concentrated to give the complex base catalyst of the present invention and the water obtained during the concentration is optionally recycled to the hydrogenation stage reactor.

The powdery composite catalyst of the present invention is used in the hydrogenation reaction which comprises nickel, aluminum, and component A. Component A is at least one selected from the group consisting of Fe, Cu, Co, Mn, Cr, Mo, B and P. The amount of nickel is in the range of from 25 to 99.9 wt %, and the total amount of aluminum and component A is in the range of from 0.1 to 75 wt %. The particle size of the catalysts may vary from 40 to 300 mesh.

The component A acts as a modifying agent to modify the crystalline state of the nickel-aluminum alloy to improve the selectivity of the hydrogenation reaction and enhance the activity of powdery composite catalyst.

The powdery composite catalyst according to the present invention can be prepared by mixing powdery nickel, powdery aluminum, and component A in desired proportion, then melting them at a high temperature, followed by pulverizing them into powder of from 40 to 300 mesh after discharging and quenching, and finally, treating the powder with hydroxide aqueous solution. The concentration of hydroxide can be in the range of from 5 to 50 weight percentage. The reaction temperature is 50-90° C.

In order to improve the recovery of the hydrogenation catalyst, the present invention provides a magnetic separator coupled with the use of at least iron as the modifying agent, component A, to increase the ferromagnetism of the powdery composite catalysts and recover the powdery composite catalyst using the ferromagnetism thereof. Therefore, in a preferred embodiment of the present invention, the powdery composite catalyst of the present invention may be prepared by taking powdery nickel, powdery aluminum, powdery iron, and optional other modifying agent A, which is selected from the group consisting of Cu, Cr, Co, Mn, Mo, B and P, in desired proportion; melting them into alloy in an induction furnace; ejecting the molten alloy using gas pressure through a nozzle to a copper drum rotating at high speed to quench quickly the alloy with cooling speed being as high as $10^5$-$10^6$ K/sec; pulverizing the cooled alloy using a ball mill into powder of from 40 to 300 mesh, preferably from 100 to 200 mesh; and finally, treating the powder with 5 to 50 wt.-% hydroxide aqueous solution at a temperature of 50 to 90° C.

According to the preferred embodiment of the present invention, hydrogenation reaction can be carried out as follows: condensation liquid from the previous step, hydrogenation solvent, powdery composite catalyst recovered and, if necessary, complementary fresh powdery composite catalyst are fed to first-stage, second-stage, and optionally high-stage hydrogenation reactors by a solid-liquid conveyer, and hydrogen gas is bubbled into the reactors from the bottom of the reactors via a hydrogen gas circulator, to carry out the hydrogenation reaction under the above hydrogenation reaction conditions to form crude hydrogenation liquid containing 4-aminodiphenylamine. The powdery composite catalyst entrained out by crude hydrogenation liquid is separated by a settling vessel and a magnetic separator. Solid-liquid phase, which separates from hydrogenation liquid and contains high concentration of the powdery composite catalyst, enters into the first reactor to be reused through a mixed solid-liquid conveying device. At the same time, hydrogenation liquid containing 4-aminodiphenylamine is obtained.

The powdery composite catalyst according to the present invention is a solid-state material during the hydrogenation. In industry, the hydrogenation catalyst is typically circulated via a pump, however, when a pump is used to convey a catalyst containing a high concentration of powdery metal, pump cavity is easily damaged and the transportation effect is also not good. The present invention provides the use of a Venturi-like solid-liquid conveying device, and circulation of the powdery composite catalyst in hydrogenation system is achieved through a pump-free circulation performed by skillfully employing the power of the pump for feeding condensation solution, so that the loss of catalyst is significantly reduced, and the concentration of catalyst in condensation solution is significantly enhanced.

According to a preferred embodiment, in continuous hydrogenation process, the powdery composite catalyst in crude hydrogenation liquid is recovered through sedimentation and magnetic separator and recycled via Venturi type solid-liquid conveying device, and circulating hydrogen gas is bubbled into the reactors. The whole hydrogenation step is conducted in a complete mixing flow mode by continuously feeding stock into multistage reactors in series. The hydrogenation solvents can be the recovered and reused.

(3) Separation I.

The hydrogenation liquid having part of the powdery composite catalyst recovered through sedimentation and magnetic separator enters into the separation I process stage reactor, where the residual powdery composite catalyst in the hydrogenation liquid is recovered from hydrogenation liquid by filtration, and circulated back to the hydrogenation process stage directly or after being at least partially regenerated.

In the hydrogenation reaction of the present invention, with optionally continuously renewing a minor amount of hydrogenation catalyst, the catalyst concentration in the reaction system can always maintain at high level. Such a method of recycling catalyst can always and stably maintain the total activity of catalyst in the system at a higher level and avoid the problem that catalyst activity gradually decreases suffered by the processes employing fixed bed catalyst. The use of magnetic separator facilitates the recovery of the catalyst, and the designing and application of mixed solid-liquid conveying device makes powdery composite catalyst circulating in the hydrogenation system.

In the present invention, deactivation of catalyst is usually caused by the inorganic matter or organic carbon deposition clog pores of the catalyst, so that the active sites of the catalyst are covered, and thereby the activity of the catalyst decreases. Therefore, the present invention employs washing with a high concentration base solution, for example, 5-50 wt % aqueous solution of alkali metal hydroxide in combination with ultrasonic oscillation to regenerate the catalyst. Ultrasonic oscillation facilitates to get rid of the inorganic or organic carbon deposition, while the high concentration base solution can dissolve the aluminum, which isn't dissolved in the first base dissolution, in the catalyst to form new loose pore structures, thereby increasing the activity of the catalyst.

The present invention provides sedimentation and magnetic separator to recover magnetic hydrogenation catalyst, and design a Venturi type mixed solid-liquid conveying device to convey the catalyst back to hydrogenation reactor using the force of feeding the stocks, thereby achieving the circulation of powdery composite catalyst. The inventors also take out the catalyst after filtration to regenerate it to restore its initial activity. By the two measures, the consumption of catalyst is significantly reduced, and the activity and life time of catalyst are improved.

(4) Separation II.

The filtrate is extracted with extracting agent and co-extracting agent to obtain an organic phase and an aqueous phase. The organic phase is conveyed to separation II process. The aqueous phase is subjected to one-stage or multistage concentration to give the complex base catalyst of the present invention, which is recycled back to the condensation process.

Specifically, in the practice of the present invention, water is used as an extracting agent and the volume ratio of water to hydrogenation liquid can vary from 0.5:1 to 5:1, preferably from 0.8:1 to 1.2:1. Organic polyethers is used as co-extracting agent, and examples includes, but not limited to, polyethylene glycol ethers, such as polyethylene glycol dimethyl ether having a molecular weight of from 200 to 1000, polyethylene glycol diethyl ether having a molecular weight of from 200 to 1000, and polyethylene glycol methyl ethyl ether having a molecular weight of from 200 to 1000; polypropylene glycol ethers, such as polypropylene glycol dimethyl ether having a molecular weight of from 200 to 1000, polypropylene glycol diethyl ether having a molecular weight of from 200 to 1000, and polypropylene glycol methyl ethyl ether having a molecular weight of from 200 to 1000; fatty alcohol polyoxyethylene ethers, such as those wherein the fatty alcohol has 12 to 18 carbon atoms and polymerization degree of polyoxyethylene is from 3 to 15. The volume ratio of the co-extracting agent to water is in a range of from 0.0001:1 to 0.005:1. Pressure during extraction can be in a range of from 0.005 to 0.1 MPa, extraction temperature can be in a range of from 0 to 80° C., and extraction time can vary from 2 to 5 h. Supernatant aqueous phase containing hydrogenation solvent and complex base catalyst and organic phase mainly containing aniline, 4-aminodiphenylamine, and a minor amount of organic impurities are obtained after separation.

Figure 2:
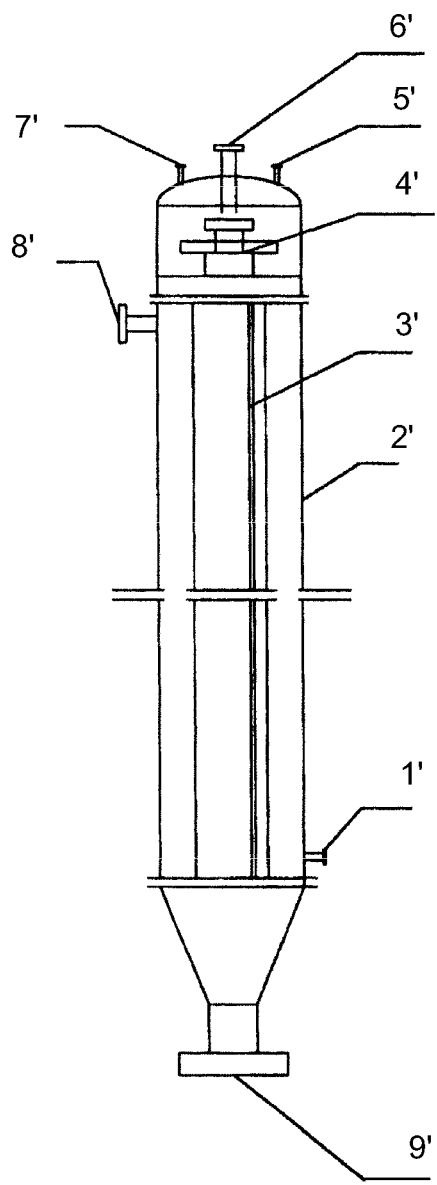
FIG. 2 is a schematic diagram illustrating a gas-aid falling film evaporator used in an embodiment of the process of the present invention. The reference numbers are: 1'—condensed water outlet; 2'—shell pass; 3'—tube pass; 4'—distributing tray; 5',7'—flow-aiding steam inlet; 6'—lower concentration aqueous phase inlet; 8'—steam inlet; 9'-higher concentration aqueous phase outlet.

Concentration of aqueous phase can be conducted using one-stage or multistage gas-aid falling film evaporator. In general, heat medium used in the concentration can be water, steam or secondary steam from the preceding stage evaporator. In the gas-aid falling film evaporator of the present invention, shell pass is heated by steam, and another part of steam enters into the tube pass from steam inlet on the top of one-stage falling film evaporator, namely flow-aiding inlet. Aqueous phase enters into the tube pass from lower concentration aqueous phase inlet of the gas-aid falling film evaporators. The direction of steam motion is the same as the direction of aqueous phase motion, and the steam is of an assistant power. Specifically, as shown in FIG. 2, the gas-aid falling film evaporators include shell pass (2'), tube pass (3'), steam inlet (8') installed on the top of shell pass (2'), condensed water outlet (1') installed at the bottom of shell pass (2'), lower concentration aqueous phase inlet (6') installed on the top of tube pass (3'), higher concentration aqueous phase outlet (9') installed at the bottom of tube pass (3'), flow-aiding steam inlet (5' and 7') installed on the top of tube pass (3') and distributing tray (4') installed at a position below the lower concentration aqueous phase inlet (6').

In the falling film evaporators, the aqueous phase, carried by the steam, passes through distributing tray and flows in film form from top to bottom in the tubes. The residence time of the aqueous phase is controlled in a range of from 2 to 60 seconds and the temperature of the aqueous phase can be in a range of from 30 to 105° C. The pressure of shell pass steam used in the concentration is in a range of from 0.005 to 0.1 MPa (absolute pressure). With the use of a gas-aid falling film evaporator and utilizing the steam to carry the aqueous phase flowing from the top to the bottom, the liquid flow rate is quickened and the residence time is controlled, at the meantime, low-boiling substances in the aqueous phase is largely evaporated at the higher temperature. Thus the decomposition of complex base catalyst containing tetraalkyl ammonium hydroxide can be minimized. If the hydrogenation solvent is an alcohol, the condensate from the condensation of evaporated substances which is a mixture of water and the alcohol can be conveyed to separation II process to recover the hydrogenation solvent. If the hydrogenation solvent is a mixture of water and an alcohol, the condensate from the condensation of evaporated substances which is a mixture of water and the alcohol can be recycled back to the hydrogenation process or conveyed to separation II process to recover the alcohol. If the hydrogenation solvent is water, the condensate from the condensation of evaporated substances which is water can be recycled back to the hydrogenation process.

In the separation II process stage of the present invention, aniline is obtained by evaporation from the extracted organic phase conveyed from separation I process stage, and the aniline is recycled back to the condensation process. The column bottoms from which most aniline is separated are conveyed to refining process. The operating pressure of the evaporator can vary from 0.005 to 0.1 MPa (absolute pressure), column bottom temperature is in a range of from 120 to 320° C., and the temperature of gas phase is in a range of from 60 to 190° C.

In the cases where the hydrogenation solvent is an alcohol or a mixture of an alcohol and water, the evaporator condensate which is obtained from the condensation of aqueous phase in separation I process is subjected to rectification to give the alcohol as hydrogenation solvent, and the alcohol is recycled back to the hydrogenation process.

(5) Refining.

The organic phase having most aniline separated in separation II process stage contains 4-aminodiphenylamine, aniline, azobenzene and phenazine, etc. In an embodiment of the present invention, the refining process is conducted through three-column continuous rectification and batch rectification, wherein the organic phase to be refined is conveyed via a pump into rectification column 1, where aniline, azobenzene and phenazine are taken out from the column top, and crude 4-aminodiphenylamine is discharged from the column bottom. The effluent from the top of rectification column 1 enters into rectification column 3, where aniline with a purity of about 99% is distilled from the top of rectification column 3 and can be directly recycled back to condensation process, and azobenzene and phenazine are left in the column bottom. Column bottoms of rectification column 1 are conveyed via a pump to rectification column 2, where the finished 4-aminodiphenylamine is distilled from the top of rectification column 2, and column bottoms of rectification column 2, after accumulating to a certain amount, are conveyed to batch still, where a minor amount of 4-aminodiphenylamine left in the bottoms is distilled off and conveyed back to rectification column 2, and the other residues are discharged from the still bottom.

In the above refining process according to the present invention, the rectification column 1 is operated at a vacuum degree of from 0.09 to 0.098 MPa, a reflux ratio of from 2:1 to 10:1, a column top temperature of from 80 to 130° C., a still temperature of from 260 to 290° C.; the rectification column 2 is operated at a vacuum degree of from 0.09 to 0.098 MPa, a reflux ratio of from 1:0.5 to 1:4, a column top temperature of from 140 to 190° C., a still temperature of from 260 to 300° C.; the rectification column 3 is operated at a vacuum degree of from 0.09 to 0.098 MPa, a reflux ratio of from 1:0.5 to 1:2, a column top temperature of from 80 to 120° C., a still temperature of from 120 to 170° C.; and the batch rectification column is operated at a vacuum degree of from 0.09 to 0.098 MPa, a column top temperature of from 235-250° C., and a still temperature of from 280 to 330° C. The still temperature of the rectification column 2 is relatively lower, thus coking of 4-aminodiphenylamine can be reduced, and 96% or more of 4-aminodiphenylamine can be distilled off at the top of rectification column 2 operated at a relatively lower still temperature, so that the amount of 4-aminodiphenylamine in the bottoms to be subjected to batch evaporation is significantly reduced.

In the process for preparing 4-aminodiphenylamine according to the present invention, the complex base catalyst and powdery composite catalyst used have lower production cost and higher catalytic activity; the whole process can be continuously carried out and is suitable for industrial scale production; the use of the complex base catalysts in condensation process significantly decreases the difficulty of operating and controlling the reaction and renders the water in the reaction system being no longer a reaction-confining factor; the decomposition of complex base catalyst is much less than that of the single tetraalkyl ammonium hydroxide catalyst;

the selection of a falling film reactor and raw material proportion improves selectivity of the reaction; there needs no solvent; the hydrogenation reaction can be carried out at a lower temperature and mild reaction conditions, and the hydrogenation catalyst is good at antitoxic performance, by-product is little, and conversion and selectivity is high; a magnetic separator is used to recover magnetic powdery composite catalyst during hydrogenation process; the hydrogenation catalyst is conveyed back to hydrogenation reactor via a Venturi type mixed solid-liquid conveying device using the force of feeding stocks; catalyst can be regenerated by chemical and/or physical methods, and thus the consumption of catalyst is reduced; the complex base catalyst is recovered after hydrogenation, and water containing co-extracting agent is used as extracting agent to separate the complex base catalyst; the aqueous phase is concentrated by one-effect or multi-effect gas-aid falling film evaporator to recover the complex base catalyst; the whole process is continuous and the operational strength is low; no corrosive liquid is produced, and environment pollution is almost eliminated. The purity of 4-aminodiphenylamine can exceed 99 wt %, and the yield in the whole industrial production process can be over 95 wt %.

4-aminodiphenylamine can be reductively alkylated to make alkylated p-phenylenediamines by known methods, for examples, as depicted in WO 93/00324, at page 13, lines 12 to 24, the contents of which is incorporated herein by reference.

EXAMPLES

The following examples further describe the present invention, but do not make limitation to the scope of the present invention in any way.

Example 1

Preparation of a Complex Base Catalyst

To a 1000 ml three-necked flask equipped with a condenser and a stirrer were added 227.5 g of 20 wt.-% aqueous solution of tetramethyl ammonium hydroxide (0.5 mol), 10 g (0.25 mol) of sodium hydroxide and 346 g of 30 wt.-% aqueous solution of tetramethyl ammonium carbonate (0.5 mol). The mixture was homogeneously stirred at 72-77° C. to give a complex base catalyst having a concentration of 27.3 wt.-%.

Example 2

Preparation of a Powdery Composite Catalyst 46 g of powdery nickel, 51 g of powdery aluminum, and 3 g of powdery iron were taken and mixed, then molten into alloy state in an induction furnace. The molten alloy was ejected using gas pressure through a nozzle to a copper drum rotating at high speed to be quenched quickly with cooling speed being as high as $10^5$-$10^6$ K/sec. The cooled alloy was pulverized using a ball mill, and 99.7 g of powder of from 40 to 300 mesh were obtained by sieving. 375 g of 20 wt.-% sodium hydroxide aqueous solution was charged into a 500 ml three-necked flask equipped with a thermometer and a stirrer, and the above powder is slowly added thereto. The mixture was stirred at 60° C. for 4 h, then the solid was washed with deionized water until neutral to give a powdery composite catalyst.

Example 3

Under vacuum condition, feeding pumps of the above complex base catalyst, aniline and nitrobenzene were simultaneously switched on and adjusted to such flow rate as aniline 150 kg/h, nitrobenzene 30 kg/h and the complex base catalyst 200 kg/h. The aniline, nitrobenzene and complex base catalyst were continuously fed into a falling film reactor to be heated and allowed to condense. Condensation liquid in the falling film reactor was discharged from the bottom into a first reactor to proceed with condensing. Part of condensation liquid from the bottom of the first reactor was conveyed back to the falling film reactor via a circulating pump, forming a local circulating system. Ethanol vapor at 78-90° C. was used as the heat medium of the falling film reactor. Reaction temperature was controlled as 75° C., pressure was controlled as 0.008 MPa (absolute pressure) and flow rate of the circulating liquid was controlled as 1 $m^3$/h. The reactants overflowed from the first reactor into a second-stage reactor. The process conditions of the second-stage reactor, such as operational temperature and pressure, were identical with that of the first reactor. The total residence time of the reactants in the falling film reactor, first reactor and second-stage reactor was controlled as 5 h. Once the condensation reaction became stable, the complex base catalyst recovered according to the procedure as described in the following examples could be used, with only a minor amount of fresh complex base catalyst prepared according to example 1 being replenished, so that the molar ratio of hydroxide ion to nitrobenzene was controlled not less than 1:1. The effluent of the second-stage reactor was found to contain not larger than 0.1 wt.-% of nitrobenzene, 24.9 wt.-% of water and 16.1 wt.-% of 4-nitrosodiphenylamine and 4-nitrodiphenylamine.

Example 4

Under vacuum condition, feeding pumps of the complex base catalyst, aniline and nitrobenzene were simultaneously switched on and adjusted to such flow rate as aniline 150 kg/h, nitrobenzene 30 kg/h and the complex base catalyst 200 kg/h. The aniline, nitrobenzene and complex base catalyst were continuously fed into a falling film reactor to be heated and allowed to condense. Condensation liquid in the falling film reactor was discharged from the bottom into a first reactor to proceed with condensing. Part of condensation liquid from the bottom of the first reactor was conveyed back to the falling film reactor via a circulating pump, forming a local circulating system. Ethanol vapor at 78-90° C. was used as the heat medium of the falling film reactor. Reaction temperature was controlled as 75° C., pressure was controlled as 0.008 MPa (absolute pressure) and flow rate of the circulating liquid was controlled as 1 $m^3$/h. The reactants overflowed from the first reactor into a second-stage reactor. The process conditions of the second-stage reactor, such as operational temperature and pressure, were identical with that of the first reactor. The total residence time of the reactants in the falling film reactor, first reactor and second-stage reactor was controlled as 5 h. Once the condensation reaction became stable, the complex base catalyst recovered was used, with sodium hydroxide and tetraalkyl ammonium salt (i.e. tetramethylammonium carbonate according to Example 1) in a molar ratio of 1:1 being replenished, so that the molar ratio of hydroxide ion to nitrobenzene was controlled not less than 1:1. The effluent of the second-stage reactor was found to contain not larger than 0.1 wt.-% of nitrobenzene, 15.6 wt.-% of water and 17.6 wt.-% of 4-nitrosodiphenylamine and 4-nitrodiphenylamine.

Example 5

Hydrogenation

The condensation liquid as prepared in Example 3 was conveyed to hydrogenation reactor after filtration. Hydrogen gas was used to replace the atmosphere of the system and pressurize to 1.3 MPa. A hydrogen gas circulator was switched on and flow rate of circulating hydrogen gas was maintained at 1 Nm$^3$/h. The circulating hydrogen gas was bubbled into the hydrogenation reactor to improve the gas-liquid mass transfer effect during reaction. The flow rate of condensation liquid of nitrobenzene and aniline was controlled as 306 kg/h, and the flow rate of methanol was controlled as 60 l/h (48 kg/h). The hydrogenation feedstock was fed into a first-stage hydrogenation reactor equipped with a sealed magnetic stirrer and a cooling and heating system, and powdery composite catalyst above prepared was added simultaneously so that the solid-liquid ratio by weight was 6:100. Hydrogenation-reduced liquid overflowed from the first reactor into a second-stage reactor, then into a third-stage reactor, finally into a settler. The reaction temperature was 75-80° C., pressure was 1.3 MPa and total residence time was 5 h. The powdery composite catalyst was recovered as much as possible under the action of a magnetic separator. Solid-liquid mixture containing higher concentration of solid catalyst at the bottom of the settler was returned to the first-stage hydrogenation reactor via a Venturi type solid-liquid conveying device using the force of feeding stocks. The activity of the catalyst in the hydrogenation reaction was judged by monitoring the endpoint of reducing reaction, and thus it could be determined whether powdery composite catalyst for hydrogenation reaction was replenished.

The hydrogenation-reducing liquid was measured by high performance liquid chromatograph (HPLC) and was found not containing 4-nitrodiphenylamine and 4-nitrosodiphenylamine.

Example 6

Separation I

The hydrogenation liquid as prepared in Example 5, after settling and magnetic separating the powdery composite catalyst, was subjected to filtration to recover extremely fine powdery composite catalyst which was not recovered by magnetic separation. The powdery composite catalyst recovered by filtration was recycled back to the hydrogenation process after regeneration.

Hydrogenation-reduced liquid containing no solid catalyst was continuously fed at a flow rate of 360 l/h to top of an extraction column via a metering pump, and extracting agent water having the same flow rate of 360 l/h and co-extracting agent polyethylene glycol dimethyl ether with a molecular weight of 400-800 having a flow rate of 0.4 l/h were continuously fed to the bottom of the extraction column. After extraction, aqueous phase was discharged from the column top and organic phase was discharged from the column bottom. The extraction time was 3 h and extraction pressure was atmospheric pressure. Methanol and the complex base catalyst in the hydrogenation-reduced liquid were extracted by water to aqueous phase. An aqueous phase was obtained at an amount of 540 l/h and organic phase was obtained at an amount of 180 l/h.

The aqueous phase, after preheated to 80° C., was fed at a flow rate of 540 l/h via a metering pump to top of a gas-aid falling film evaporator whose shell pass was heated with 120° C. steam. The residence time of the stuff in the evaporator was 10 sec. The primary concentrated liquid was conveyed to a second-stage shell-and-tube falling film evaporator under 0.1 MPa (absolute pressure) and the residence time of the stuff in this evaporator was 10 sec. The temperature of gas-liquid mixture discharged from second-stage falling film evaporator was 80-95° C. After separating via secondary gas-liquid separator, recovery ratio of the complex base catalyst in the whole concentrating process might be as high as 99.7%. The complex base catalyst was recycled back to the condensation process.

Example 7

Separation II

The gas phase evaporated from the falling film evaporators condensed to give a methanol-water solution containing about 28 wt. % of methanol. The methanol-water solution was continuously pumped to a rectification column to conduct separation, thus methanol having a purity of more than 99 wt. % was obtained from column top and could be reused in the hydrogenation process, and water was in the column bottom. The water in the column bottom was measured by gas chromatography (GC) and it was found that the content of methanol therein was less than 0.3 wt. %

The organic phase from extraction operation was fed to a shell-and-tube rising film evaporator to separate most aniline. Operational pressure of the rising film evaporator was 0.01 MPa (absolute pressure), and 180° C. steam was used to heat in the shell pass. A gas phase at 75-105° C. and a liquid phase at 160° C. were gained from a gas-liquid separator located on the top of the rising film evaporator. The gas phase material after condensation was measured by chromatography and the content of aniline was found as high as 99 wt. %. Most of aniline was distilled during the process, and the distilled aniline could be recycled back to the condensation process as the raw material of condensation reaction. Liquid phase material was the crude product of 4-aminodiphenylamine, containing 78.1 percent of 4-aminodiphenylamine, 21.75 percent of aniline and the balance amount of other organic impurities.

Example 8

Refining

The crude product of 4-aminodiphenylamine (containing 78.1% 4-aminodiphenylamine, 21.75% aniline, 0.05% azobenzene, and 0.1% phenazine) was continuously fed to rectification column 1 at a flow rate of 120 kg/h via a gear pump. The temperature of still was controlled as 270° C., the temperature of column top was controlled as 110° C., vacuum degree was controlled as 0.094 MPa and reflux ratio was controlled as 5:1. Light components, i.e. aniline, azobenzene and phenazine, were taken out from the column top at a flow rate of about 26.2 kg/h, and conveyed to rectification column 3.

The rectification column 3 was operated at conditions of still temperature of 150° C., column top temperature of 90° C., vacuum degree of 0.094 MPa and reflux ratio of 1:1. Aniline was distilled off from column top at a flow rate of 24 kg/h, and azobenzene and phenazine were left in column bottom.

Column bottoms of the rectification column 1 were conveyed to rectification column 2. The rectification column 2 was operated at conditions of still temperature of 280° C., column top temperature of 170° C., vacuum degree of 0.097 MPa and reflux ratio of 1:1. The finished 4-aminodiphenylamine was obtained at the column top of the rectification column 2.

Column bottoms of the rectification column 2 were conveyed to batch still. The batch still was operated at conditions of kettle temperature of 285-320° C., vacuum degree of 0.094

MPa and top temperature of 235-250° C., to distill off the residual 4-aminodiphenylamine, which was recycled back to the rectification column 2 to be further distilled. The whole refining process of 4-aminodiphenylamine was continuously carried out. The finished 4-aminodiphenylamine product obtained had a purity of 99.1%, a melting point of 72° C. and a solidifying point of 72.4° C. The yield of the process step in industrial production was 95.1%.

Example 9

Process for Regenerating Catalyst 20 g of powdery composite catalyst, which was recovered by filtration of the hydrogenation liquid, was charged into a 100 ml three-necked flask equipped with a stirrer and a thermometer. 20 ml of 40% aqueous solution of sodium hydroxide was added thereto. While stirring, the mixture was heated to 90° C. and maintained at that temperature for 1 h. At the end of the reaction, the catalyst was subjected to ultrasonic washing for 30 min in a washing tank, followed by washing with water for multiple times until the pH of the washing water was 7-8. The gained solid was regenerated powdery composite catalyst.

Example 10

Preparation of a Complex Base Catalyst

To a 500 ml three-necked flask equipped with a condenser and a stirrer were added 230 g of water, followed by adding 91 g of pentahydrated tetramethyl ammonium hydroxide (containing 0.5 mol of tetramethyl ammonium hydroxide), 20 g (0.5 mol) of sodium hydroxide and 70 g of trimethylhydroxyethyl ammonium chloride (0.5 mol). The mixture was homogeneously stirred at 75±2° C. to give a complex base catalyst having a concentration of 32.85 wt.-%.

Example 11

Preparation of a Complex Base Catalyst

To a 500 ml three-necked flask equipped with a condenser and a stirrer were added 230 g of water, followed by adding 91 g of pentahydrated tetramethyl ammonium hydroxide (containing 0.5 mol of tetramethyl ammonium hydroxide), 20 g (0.5 mol) of sodium hydroxide and 74.5 g of tetramethyl ammonium methylcarbonate ($[(CH_3)_4N]^+[CO_3CH_3]^-$)(0.5 mol). The mixture was homogeneously stirred at 75±2° C. to give a complex base catalyst having a concentration of 33.7 wt.-%.

Example 12

To a 500 ml four-necked flask equipped with a stirrer and a water segregator and a condenser were added 150 g of water, followed by adding 91 g of pentahydrated tetramethyl ammonium hydroxide (containing 0.5 mol of tetramethyl ammonium hydroxide), 20 g (0.5 mol) of sodium hydroxide and 74.5 g of tetramethyl ammonium methylcarbonate ($[(CH_3)_4N]^+[CO_3CH_3]^-$)(0.5 mol). Then 25 g of benzene were added thereto, and the mixture was heated to reflux. There were water layer and oil layer in the water segregator. Oil layer was returned to the four-necked flask and water layer was separated out until there was no water in distilled liquid. An anhydrous form of complex base catalyst was obtained.

Example 13

Preparation of Tetramethylammonium

Methyl-Carbonate ($[(CH_3)_4N]^+[CO_3CH_3]^-$)

To a 1.5 L autoclave equipped with a stirrer and a heating means were added 90 g (1.0 mol) of dimethyl carbonate, 59 g (1.0 mol) of trimethyl amine and 510 g (15 mol) of methanol. Stirring was initiated after the autoclave was sealed. The autoclave was heat to 140° C., and pressure was 1.5 MPa. The reaction was kept at 140° C. for 4 h. Then the reaction mixture was cooled to 50° C. and discharged into a 1 L three-necked flask. Part of methanol was removed from the solution of tetramethylammonium methyl-carbonate in methanol thus obtained under vacuum, and then the solution was cooled to ambient temperature. White crystal precipitated out. The crystal was filtrated, oven dried and recrystallized from methanol, to give 119.5 g of tetramethylammonium methyl-carbonate having a purity of 99.2% as measured by chromatography. The yield was 80.2%.

Example 14

92.5 g (1 mol) of 1-chloro-2,3-epoxy propane, 3 g (1 mol) of N-methyl diethanolamine, 2 g of sodium hydroxide and 700 g of water were charged into an autoclave with a stirrer, a heating means and a thermometric means. With stirring, the mixture was gradually heated to 120° C., then gaseous ethylene oxide was continuously passed into the autoclave to maintain a reactor pressure of 0.3 MPa until the quantity of ethylene oxide passed into reached 150 g. The reaction continued for further 2 h at that temperature, to give $ClCH_2[CH_2CH_2O]_{2-5}$—H. 60 g of gaseous trimethylamine were passed thereto. The autoclave was heat to 140° C., and pressure was 1.5 MPa. The reaction was maintained at that temperature for 4 h. Then the mixture was cooled to room temperature. After conventionally dehydrating and drying, 105 g of N,N,N-trimethyl-N-ethoxylated (1-4 moles of ethylene oxide) propyl ammonium chloride was obtained.

Example 15

Preparation of Tetramethyl Ammonium Hydroxide

To a 1.5 L autoclave equipped with a stirrer and a heating means were added 90 g (1.0 mol) of dimethyl carbonate, 59 g (1.0 mol) of trimethyl amine and 510 g (15 mol) of methanol. Stirring was initiated after the autoclave was sealed. The autoclave was heated to 140° C., and pressure was 1.5 MPa. The reaction was kept at 140° C. for 4 h. Then the reaction mixture was cooled to room temperature and discharged into a 1 L three-necked flask. A slurry consisting of 148 g (2.0 mol) of calcium hydroxide and 350 g of water was added thereto. Methanol was distilled off by heating over 8 h while stirring. 355 g of tetramethyl ammonium hydroxide solution was obtained after filtration. The content of tetramethyl ammonium hydroxide was found as 24.4% and the total reaction yield was 95.2%.

Example 16

Preparation of Tetraethyl Ammonium Hydroxide

To a 1.5 L autoclave equipped with a stirrer and a heating means were added 154 g (1.0 mol) of diethyl sulfate, 101 g (1.0 mol) of triethyl amine and 690 g (15 mol) of ethanol.

Stirring was initiated after the autoclave was sealed. The autoclave was heat to 140° C., and pressure was 1.0 MPa. The reaction was kept at 140° C. for 4 h. Then the reaction mixture was cooled to room temperature and discharged into a 1 L three-necked flask. 80 g (2.0 mol) of sodium hydroxide was added thereto. The reaction mixture was heated to 45° C. for 4 h while stirring. After filtration, part of ethanol was distilled off from the filtrate. Then 500 g of water was added while ethanol was distilled off (part of water was entrained out), to give 604 g of tetraethyl ammonium hydroxide solution. The content of tetraethyl ammonium hydroxide was found as 23.3 wt.-% and the total reaction yield was 95.7%.

Example 17

Effect on Reaction Imposed by the Quantity of Aniline and Nitrobenzene

A local circulating system having a total volume of 1 L was comprised of a miniature reactor equipped with a vacuum system and a temperature control system, a film reactor and a circulating pump. The system was firstly filled with aniline, and the flow of the circulating pump was set at 2 l/h. A mixture, containing nitrobenzene, aniline and the complex base catalyst prepared according to example 1 at a molar ratio of nitrobenzene to aniline to OH⁻ in the complex base catalyst of 1:1:1.8, was fed to the reactor at a flow rate of 200 ml/h. The residence time was 5 h. The system temperature was maintained as 75° C. and the system pressure was maintained as 0.008 MPa (absolute pressure). After the aniline was replaced by reaction liquid and reaction liquid was stable in composition, a sample was taken and analyzed. Nitrobenzene was substantially not detectable. The reaction selectivity was calculated according to the total mole number of 4-nitrosodiphenylamine and 4-nitrodiphenylamine generated.

The results obtained under the same conditions except that the ratio of nitrobenzene to aniline was changed were showed in table 1.

TABLE 1

Effect On Reaction by Quantities Of Aniline And Nitrobenzene

| No. | Nitrobenzene:aniline (mol/mol) | Reaction selectivity (%) |
| --- | --- | --- |
| 1 | 1:1 | 90.2 |
| 2 | 1:3 | 96.1 |
| 3 | 1:5 | 99.1 |
| 4 | 1:10 | 99.3 |

It can be seen from the data showed in table 1 that increasing the molar ratio of aniline to nitrobenzene will enhance the reaction selectivity, increase target products and reduce the by-products. However, in the practice, if the quantity of aniline is too large, the loss of aniline and the energy consumption during separation will increase.

Example 18

Effect on Condensation Reaction Imposed by Water

A continuous reactor was connected to a vacuum system and equipped with a temperature control system, and formed a local circulating system with a falling film evaporator and a circulating pump. Total volume of the reaction system was 1 L. The system was firstly filled with aniline, and the flow of the circulating pump was set at 2 l/h. A mixing liquid containing nitrobenzene, aniline and the complex base catalyst at a molar ratio of nitrobenzene to aniline to OH⁻ in the complex base catalyst of 1:7:1.15 was fed to the reactor at a certain flow. The system temperature was maintained as 75° C. and the system pressure was maintained as 0.008 MPa (absolute). After the aniline was replaced by reaction liquid and reaction liquid was stable in composition, the feeding flow rate of the reaction mixture was varied to adjust the residence time. The water contents of reaction effluent, measured when the measured content of nitrobenzene was equal to or less than 0.1% and calculated yield based on 4-nitrosodiphenylamine and 4-nitrodiphenylamine generated was 97%, were listed below.

| No. | Molar ratio of three components in complex base catalyst Tetramethyl ammonium hydroxide:N,N-dimethyl-N,N-bis(ethoxylated (1-4 moles of ethylene oxide) propyl) ammonium carbonate:sodium hydroxide | Water content in product (%) |
| --- | --- | --- |
| 1 | 5:2:2 | 5.1 |
| 2 | 3:2:2 | 10.2 |
| 3 | 2:2:2 | 15.4 |
| 4 | 1:2:1 | 17.5 |
| 5 | 0.5:2:0.5 | 19.8 |
| 6 | Tetramethyl ammonium hydroxide is used as catalyst | 1.2 |

It can be seen that water content at the end of the reaction increases as the proportion of N,N-dimethyl-N,N-bis(ethoxylated (1-4 moles of ethylene oxide) propyl) ammonium carbonate in the complex catalyst increases. Namely, with the use of a complex base catalyst according to the present invention, the range of permitted water content in the reaction mixture at the end of reaction is greatly enlarged, that is, the yield is good enough even when there is a higher content of water in the reaction system. The less the water content is in the later phase of the reaction, the lower the dehydration efficiency is, thus reaction difficulty is reduced in the process according to the present invention. If only the tetramethyl ammonium hydroxide is used as catalyst, the yield is not 97% until the water content of reaction mixture is reduced to 1.2% by dehydration, which imposes difficulty to the reaction control and increases the power consumption.

Example 19

Anhydrous complex catalyst prepared in example 12 and 651 g of aniline were charged into a four-necked flask with stirring device and thermometer. With stirring, the temperature was elevated to 75° C. and pressure was reduced to 0.008 MPa (absolute pressure). Aniline was returned to the four-necked flask after demixing of the water-aniline azeotrope distilled until the water content in the system is less than 0.5%. 123 g of nitrobenzene was dropwise added over 2 h, then the dehydrating was continued for 4 h. It was found via chromatographic analysis that the yield of 4-nitrosodiphenylamine and 4-nitrodiphenylamine was 97.4% and the water content in the system was less than 0.5%.

Example 20

Comparison of Continuous Film Reaction and Complete Mixing Reaction

Continuous film reactions and complete mixing reactions were conducted under the following conditions: molar ratio of aniline to nitrobenzene to OH⁻ in complex base catalyst was controlled as 7.5:1:1, reaction temperature was 75° C., reaction time was 5 h, and reaction pressure was 0.005 MPa (absolute pressure). Results were listed in Table 2 and Table 3.

TABLE 2

Results of Complete Mixing Reactions

| No. | Conversion rate of nitrobenzene % | Yield % |
|---|---|---|
| 1 | 98.1 | 94.6 |
| 2 | 98.3 | 95.1 |
| 3 | 98.1 | 94.8 |

TABLE 3

Results Of Continuous Film Reactions

| No. | Conversion rate of nitrobenzene % | Yield % |
|---|---|---|
| 1 | 99.2 | 97.6 |
| 2 | 99.9 | 98.1 |
| 3 | 99.5 | 97.8 |

Example 21

Batch Hydrogenating Example 500 g of condensation liquid containing 17.5 weight percent of 4-nitrosodiphenylamine and 3.0 weight percent of 4-nitrodiphenylamine was charged into a 1 L autoclave with stirring device and temperature control device. 150 g of ethanol and 5 g of the powdery composite catalyst prepared in example 1 were added thereto. The system atmosphere was replaced with hydrogen gas for three times, and then the system was pressurized to 0.8 MPa. While stirring, the reaction mixture was heated to 100° C. and maintained at this temperature for 4 h. At the end of the reaction, the mixture was cooled, and then discharged after pressure release. The reaction liquid was analyzed via HPLC, and was found containing no 4-nitrosodiphenylamine and 4-nitrodiphenylamine but 14.6% of 4-aminodiphylamine (chromatograph content).

Comparison of Powdery Composite Catalyst and Noble Metal Catalyst

Pd/C catalyst with 5 wt. % of palladium was compared with the powdery composite catalyst according to the present invention. Experiments were carried out under the same conditions as described in above batch hydrogenating example. The quantity of catalysts used was the same, and both Pd/C catalyst and powdery composite catalyst were recovered and reused after the reaction. Within 21 times of reuse, 4-nitrosodiphenylamine was undetectable in both reaction liquids. However, at the twenty-first time of reuse, the reaction liquid obtained by using Pd/C catalyst was found containing 0.1 wt. % of 4-nitrodiphylamine while the reaction liquid obtained by using the powdery composite catalyst according to the present invention was found containing no 4-nitrodiphylamine. The results showed that the antitoxic performance of the powdery composite catalyst according to the present invention was better than that of the noble metal catalyst.

We claim:

1. A process for preparing alkylated p-phenylenediamine, comprising
reacting aniline and nitrobenzene in a condensation reaction in presence of a complex base catalyst to obtain 4-aminodiphenylamine intermediates,
hydrogenating the 4-aminodiphenylamine intermediates to 4-aminodiphenylamine in presence of a hydrogenation catalyst, and
reductively alkylating the 4-aminodiphenylamine to alkylated p-phenylenediamine,
wherein the aniline is in excess to the nitrobenzene in the condensation reaction;
the complex base catalyst comprises a tetraalkyl ammonium hydroxide and a salt thereof, and an alkali metal hydroxide or oxide;
molar ratio of total molar amount of the tetraalkyl ammonium hydroxide and the salt thereof to molar amount of the alkali metal hydroxide or oxide in the complex base catalyst is in a range of 2.5 to 5:1, and
the salt of the tetraalkyl ammonium hydroxide is represented by

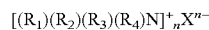
$[(R_1)(R_2)(R_3)(R_4)N]^+{}_n X^{n-}$ wherein $R_1$, $R_2$, $R_3$, and $R_4$, identical or different, respectively, is an alkyl having from 1 to 4 carbon atoms and said alkyl being optionally substituted by a hydrophilic substitute; and $X^{n-}$ is selected from the group consisting of carbonate radical, bicarbonate radical, $C_1$-$C_2$-alkyl carbonate radical, and $C_1$-$C_2$-alkyl sulfate radical; n is 1 or 2.

2. The process of claim 1, further comprising
separating, recovering, and reusing the excess aniline.

3. The process of claim 1, further comprising
separating, recovering, and reusing the complex base catalyst.

4. The process of claim 1, further comprising
recovering and reusing the hydrogenation catalyst.

5. The process of claim 1, wherein the hydrogenation catalyst is a powdery catalyst comprising nickel, aluminum, and a component A that is selected from the group consisting of Fe, Cu, Co, Mn, Cr, Mo, B, P, and a mixture thereof.

6. The process of claim 1, further comprising
refining the 4-aminodiphenylamine before the reductive alkylation step.

7. The process of claim 1, wherein the aniline and the nitrobenzene are continuously fed into and reacted in a local circulating reaction system comprising a falling film reactor and a first-stage reactor to avoid back-mixing of the aniline and the nitrobenzene with the 4-aminodiphenylamine intermediates.

8. The process of claim 1, wherein the hydrogenation catalyst is a powdery composite catalyst comprising iron as a modifying agent with ferromagnetism and has a particle size of 40 to 300 mesh.

9. The process of claim 1, wherein decomposition rate of the complex base catalyst is less than 0.5% in the condensation reaction.

10. A process for preparing alkylated p-phenylenediamine, comprising
reacting aniline and nitrobenzene in a condensation reaction in presence of a complex base catalyst to obtain 4-aminodiphenylamine intermediates,
hydrogenating the 4-aminodiphenylamine intermediates to 4-aminodiphenylamine in presence of a hydrogenation catalyst, and reductively alkylating the 4-aminodiphenylamine to alkylated p-phenylenediamine,
wherein the aniline is in excess to the nitrobenzene in the condensation reaction;
the complex base catalyst comprises a tetraalkyl ammonium hydroxide, an alkali metal hydroxide or oxide, and a salt of the tetraalkyl ammonium hydroxide;
the tetraalkyl ammonium salt is represented by

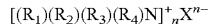
$$[(R_1)(R_2)(R_3)(R_4)N]^+{}_n X^{n-}$$

wherein $R_1$, $R_2$, $R_3$, and $R_4$, identical or different, respectively, is an alkyl having from 1 to 4 carbon atoms and said alkyl being optionally substituted by a hydrophilic substitute; and $X^{n-}$ is selected from the group consisting of halide ion, sulfate radical, carbonate radical, phosphate radical, bicarbonate radical, bisulfate radical, $C_1$-$C_2$-alkyl carbonate radical, and $C_1$-$C_2$-alkyl sulfate radical; n is a value of from 1 to 2, and molar ratio of the tetraalkyl ammonium hydroxide to the alkali metal hydroxide or oxide to the tetraalkyl ammonium salt in the complex base catalyst is selected from the group consisting of 1:0.5:1, 1:1:1, 5:2:2, 0.5:0.5:2, 3:2:2, and 1:1:2.

11. The process of claim 10, further comprising separating, recovering, and reusing the excess aniline.

12. The process of claim 10, further comprising separating, recovering, and reusing the complex base catalyst.

13. The process of claim 10, further comprising recovering and reusing the hydrogenation catalyst.

14. The process of claim 10, wherein the hydrogenation catalyst is a powdery catalyst comprising nickel, aluminum, and a component A that is selected from the group consisting of Fe, Cu, Co, Mn, Cr, Mo, B, P, and a mixture thereof.

15. The process of claim 10, further comprising
refining the 4-aminodiphenylamine before the reductive alkylation step.

16. The process of claim 10, wherein the aniline and the nitrobenzene are continuously fed into and reacted in a local circulating reaction system comprising a falling film reactor and a first-stage reactor to avoid back-mixing of the aniline and the nitrobenzene with the 4-aminodiphenylamine intermediates.

17. The process of claim 10, wherein the hydrogenation catalyst is a powdery composite catalyst comprising iron as a modifying agent with ferromagnetism and has a particle size of 40 to 300 mesh.

18. The process of claim 10, wherein decomposition rate of the complex base catalyst is less than 0.5% in the condensation reaction.

* * * * *